(12) United States Patent
Das et al.

(10) Patent No.: US 11,313,811 B2
(45) Date of Patent: Apr. 26, 2022

(54) DYNAMIC DETERMINATION OF IRRIGATION-RELATED DATA USING MACHINE LEARNING TECHNIQUES

(71) Applicant: International Business Machines Corporation, Armonk, NY (US)

(72) Inventors: Kamal Das, New Delhi (IN); Jagabondhu Hazra, Bangalore (IN); Ranjini Bangalore Guruprasad, Bangalore (IN); Aanchal Goyal, New Delhi (IN); Sachin Gupta, New Delhi (IN)

(73) Assignee: International Business Machines Corporation, Armonk, NY (US)

( * ) Notice: Subject to any disclaimer, the term of this patent is extended or adjusted under 35 U.S.C. 154(b) by 368 days.

(21) Appl. No.: 16/728,266

(22) Filed: Dec. 27, 2019

(65) Prior Publication Data
US 2021/0199600 A1    Jul. 1, 2021

(51) Int. Cl.
*G01N 22/04*    (2006.01)
*G06N 20/00*    (2019.01)
(Continued)

(52) U.S. Cl.
CPC .......... *G01N 22/04* (2013.01); *G01N 33/246* (2013.01); *G06N 5/04* (2013.01); *G06N 20/00* (2019.01);
(Continued)

(58) Field of Classification Search
CPC .............. G01N 22/04; G01N 33/246; G01N 2033/245; G06N 5/04; G06N 20/00;
(Continued)

(56) References Cited

U.S. PATENT DOCUMENTS

| 4,922,433 A | * 5/1990 | Mark ............... G05B 19/0415 |
| | | 700/12 |
| 7,930,069 B2 | 4/2011 | Savelle, Jr. et al. |
| | (Continued) | |

FOREIGN PATENT DOCUMENTS

| CN | 105210801 B | 1/2016 |
| CN | 106718695 B | 5/2017 |
| | (Continued) | |

OTHER PUBLICATIONS

Gao et al., Irrigation Mapping Using Sentinel-1 Time Series at Field Scale. Remote Sensing, 2018.
(Continued)

*Primary Examiner* — Tung S Lau
(74) *Attorney, Agent, or Firm* — Ryan, Mason & Lewis, LLP

(57) ABSTRACT

Methods, systems, and computer program products for dynamic determination of irrigation-related data using machine learning techniques are provided herein. A computer-implemented method includes obtaining irrigation-related data pertaining to a region of interest; determining temporal values corresponding to irrigation activity at the region of interest by performing spatiotemporal analysis of the irrigation-related data; determining amounts of water utilized in connection with the irrigation activity corresponding to the temporal values by applying machine learning techniques to the irrigation-related data; determining types of irrigation activity attributed to the irrigation activity by applying machine learning techniques to the irrigation-related data and determined amounts of water; determining irrigation-related variables pertaining to the region of interest by executing a physical model using, as inputs, the determined temporal values, amounts of water, and types of irrigation activity, wherein the irrigation-related variables
(Continued)

include an extent of irrigation activity; and outputting the determined irrigation-related variables to a user.

20 Claims, 7 Drawing Sheets

(51) Int. Cl.
G01N 33/24 (2006.01)
G06N 5/04 (2006.01)
A01G 25/00 (2006.01)

(52) U.S. Cl.
CPC ........ A01G 25/00 (2013.01); G01N 2033/245 (2013.01)

(58) Field of Classification Search
CPC ........ G06N 5/003; G06N 20/20; G06N 20/10; A01G 25/00; A01G 25/167; G06Q 50/02
See application file for complete search history.

(56) References Cited

U.S. PATENT DOCUMENTS

| | | | |
|---|---|---|---|
| 9,829,871 B1* | 11/2017 | Goodman | ............ A01G 25/167 |
| 10,936,871 B2* | 3/2021 | Tran | ...................... G06F 3/0346 |
| 2007/0196517 A1* | 8/2007 | San Martin | ............ A01N 65/00 514/33 |
| 2014/0356197 A1* | 12/2014 | Hotovec | ................. F04B 49/08 417/300 |
| 2015/0040473 A1* | 2/2015 | Lankford | ............. A01G 25/092 47/58.1 SC |
| 2015/0204055 A1* | 7/2015 | Khalifeh | ................. C02F 1/008 210/137 |
| 2016/0088807 A1 | 3/2016 | Bermudez Rodriguez et al. | |
| 2018/0348714 A1* | 12/2018 | Larue | .................... A01G 25/16 |

FOREIGN PATENT DOCUMENTS

| | | |
|---|---|---|
| CN | 106815658 A | 6/2017 |
| CN | 108802728 A | 11/2018 |
| EP | 2730159 B1 | 5/2014 |

OTHER PUBLICATIONS

Bousbih et al., Soil Moisture and Irrigation Mapping in A Semi-Arid Region, Based on the Synergetic Use of Sentinel-1 and Sentinel-2 Data. Remote Sensing, 2018.

Benabdelouahab et al., Using SAR Data to Detect Wheat Irrigation Supply in an Irrigated Semi-arid Area. Journal of Agricultural Science, 11(1), Dec. 15, 2018.

* cited by examiner

DYNAMIC DETERMINATION OF IRRIGATION-RELATED DATA USING MACHINE LEARNING TECHNIQUES

FIELD

The present application generally relates to information technology and, more particularly, to data management using machine learning techniques.

BACKGROUND

Data pertaining to irrigation dates, types, and amounts can be useful for many agriculture services, such as soil moisture estimation, which affects crop yields and quality, crop advisory and field management, transportation and administration of fertilizers, etc.

Existing agricultural management approaches commonly include manually manipulating resources such as water, energy, etc. However, unstructured data, such as irrigation date information, for example, are typically not complete and/or readily available for agricultural practitioners.

SUMMARY

In one embodiment of the present invention, techniques for dynamic determination of irrigation-related data using machine learning techniques are provided. An exemplary computer-implemented method can include obtaining multiple items of irrigation-related data pertaining to at least one region of interest, and determining one or more temporal values corresponding to irrigation activity at one or more portions of the at least one region of interest by performing spatiotemporal analysis of at least a portion of the obtained irrigation-related data. Such a method also includes determining one or more amounts of water utilized in connection with the irrigation activity corresponding to the one or more determined temporal values by applying a first set of one or more machine learning techniques to at least a portion of the obtained irrigation-related data. Also, such a method includes determining one or more types of irrigation activity to be attributed to the irrigation activity corresponding to the one or more determined temporal values by applying a second set of one or more machine learning techniques to (i) at least a portion of the obtained irrigation-related data and (ii) the one or more determined amounts of water utilized in connection with the irrigation activity. Further, such a method also includes determining one or more irrigation-related variables pertaining to the at least one region of interest by executing a physical model using, as inputs, (i) the one or more determined temporal values, (ii) the one or more determined amounts of water utilized in connection with the irrigation activity, and (iii) the one or more determined types of irrigation activity to be attributed to the irrigation activity, wherein the one or more irrigation-related variables comprises at least an extent of the irrigation activity. Additionally, the method also includes outputting the one or more determined irrigation-related variables to at least one user.

Another embodiment of the invention or elements thereof can be implemented in the form of a computer program product tangibly embodying computer readable instructions which, when implemented, cause a computer to carry out a plurality of method steps, as described herein. Furthermore, another embodiment of the invention or elements thereof can be implemented in the form of a system including a memory and at least one processor that is coupled to the memory and configured to perform noted method steps. Yet further, another embodiment of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

Figure 1:
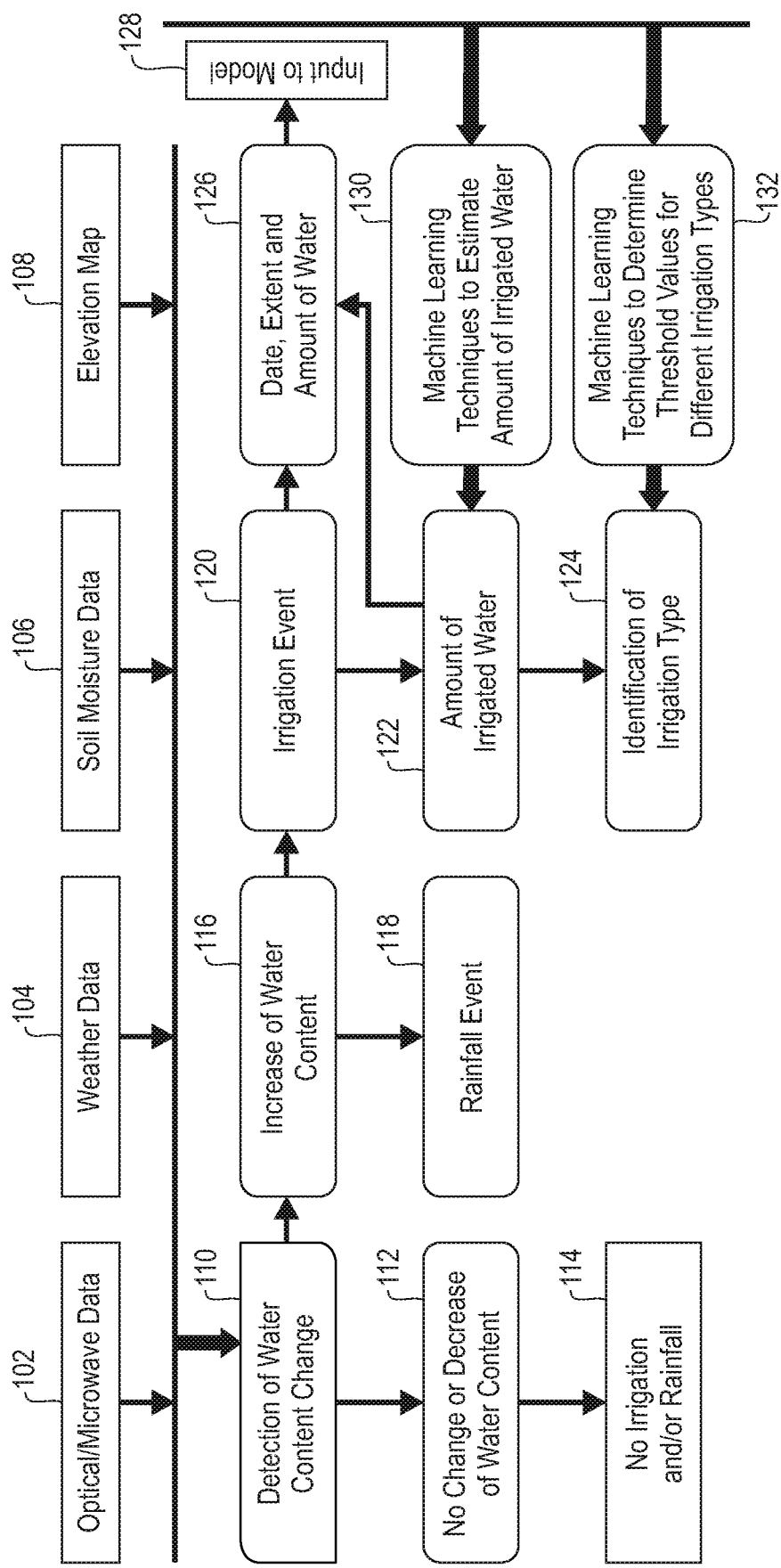
FIG. 1 is a diagram illustrating system architecture, according to an exemplary embodiment of the invention.

As described herein, an embodiment of the present invention includes dynamic determination of irrigation-related data using machine learning techniques. At least one embodiment includes estimating irrigation-related information pertaining to at least one region of interest such as, for example, irrigation date(s), extent to which irrigation activity was carried out, as well as amount and type of irrigation activity based on spatiotemporal analysis of backscattering parameters and weather data. As detailed herein, such an embodiment can include obtaining and/or monitoring, for a target region, optical and microwave multi spectral and/or hyperspectral data (e.g., from satellites that use active and/or passive sensors), weather data (e.g., rainfall data), soil moisture data (e.g., from high definition soil moisture (HDSM) sources and/or soil moisture active passive (SMAP) sources), drainage pattern data (e.g., from DEM (digital elevation models (DEMs)), etc.

Additionally, such an embodiment can also include analyzing such obtained and/or monitored data to determine and/or estimate irrigation date(s), the extent to which irrigation activity was carried out, as well as the amount and type of irrigation activity. Also, such determination can be carried out, for example, at a farm- and/or field-level with respect to the region of interest. Additionally, recorded irrigation information, if available, can be used to improve the confidence in the determinations. Such an embodiment enables improvement of the accuracy of one or more models utilized to provide estimates of irrigation-related and/or agronomic factors, while reducing dependence on sensors and monitoring systems which are cost- and maintenance-intensive.

In at least one embodiment, estimating the date(s) and extent(s) of irrigation activity includes performing spatiotemporal analysis of one or more backscattering parameters derived from microwave satellite data, rainfall data, soil moisture data, optical data, etc. Also, in one or more embodiments, estimating the amount(s) of irrigated water utilized in particular irrigation activity includes using one or more backscattering parameters on irrigation activity-related timestamps in connection with one or more machine learning techniques. Such an embodiment can include, for example, building backscatter parameters versus rainfall data, taking into account temperature, run-off, and other factors for latency in backscattering parameters (VV and VH) observation from rainfall and/or irrigation events.

As noted above and further detailed herein, backscatter is the portion of an outgoing radar signal that the target (e.g., the Earth's surface) redirects directly back towards the radar antenna of a microwave satellite system. The magnitude of the backscattered signal can depend on a variety factors such as physical factors (e.g., the dielectric constant of the surface materials (which also depends on moisture content), geometric factors (e.g., surface roughness, slopes, orientation of objects relative to the radar beam direction, etc.), and the types of landcover (e.g., soil, vegetation, man-made objects, etc.).

Additionally, in accordance with one or more embodiments, a backscattered signal is polarized, and the polarizations can be controlled between H and V as follows: (a) HH: horizontal transmit, horizontal receive; (b) HV: horizontal transmit, vertical receive; (c) VH: vertical transmit, horizontal receive; and (d) VV: vertical transmit, vertical receive. These backscattered signal polarizations are referred to herein as "backscattering parameters," and can be expressed, for example, in decibel (dB) units.

Further, in at least one embodiment, backscatter parameters can be derived, for example, from microwave satellite images via processing steps (available via tools such as, for example, a Sentinel application platform (SNAP)). Such processing steps can include, for example, applying an orbit file to correct backscattering parameters using satellite position and velocity information contained within the metadata of the image. Such processing steps can also include removing thermal noise. Microwave satellite image intensity is disturbed by additive thermal noise, particularly in the cross-polarization channel (HV/VH). Accordingly, thermal noise removal reduces noise effects in the entire image scene and results in reduced discontinuities. Additionally, such processing steps can also include removing border noise. Microwave satellite image has radiometric artifacts at the image borders, and as such, one or more embodiments includes implementing at least one border noise removal algorithm to remove low-intensity noise and invalid data on scene edges. Such processing steps can additionally include calibration, which includes a procedure that converts digital pixel values to radiometrically calibrated backscattering parameters. Further, such processing steps can include speckle filtering. Speckle, appearing in microwave satellite images as granular noise, is typically due to the interference of waves reflected from elementary scattering elements. Speckle filtering is a procedure carried out to increase image quality by reducing speckle. Processing steps can also include range doppler terrain correction, which is a correction of geometric distortions caused by topography (such as foreshortening and shadows) using a digital elevation model to correct the location of each pixel. Further, the processing steps can additionally include conversion to dB, whereby unitless backscattering parameters are converted to dB using a logarithmic transformation.

Additionally, in at least one embodiment, estimating the type(s) of irrigation activity associated with particular irrigation activity includes using optical and/or microwave data to determine one or more patterns across various contexts (using, for example, machine learning techniques to determine one or more relevant threshold values). Such contexts can include, for example, contexts pertaining to soil moisture and frequency such as surface-related information, sprinkler and/or pivot-related information, drip-related information, etc.

Further, as detailed herein, one or more embodiments include using estimations and/or determinations pertaining to irrigation activity date(s) as well as the extent(s) and amount(s) of irrigation activity as inputs into a physical model to simulate and/or estimate land surface parameters such as field-scale soil moisture, soil temperature, and/or evapotranspiration. Additionally, incorporating soil moisture data into the physical (agricultural) model reduces the uncertainty of modelled crop yields and quality when weather-related input data to the model are subject to non-trivial levels of uncertainty. Further, in one or more embodiments, estimations and/or determinations pertaining to irrigation activity date(s) as well as the extent(s), amount(s), and type(s) of irrigation activity can serve as effective inputs for pest and disease estimation.

FIG. 1 is a diagram illustrating system architecture, according to an embodiment of the invention. By way of illustration, FIG. 1 depicts input data in the form of optical/microwave data 102, weather data 104, and soil moisture data 106 (all of which encompass spatiotemporal datasets), as well as elevation map data 108, which encompasses a spatial dataset. As illustrated via component 110, a change in soil water content is detected at timestamp t using microwave data 102 at timestamps t and t−1, respectively. If the change is found to be decreasing (or if no change is found), as illustrated by component 112, an implication is made (as illustrated via component 114) that no rainfall or irrigation events have occurred. This can be further confirmed, for example, from the weather (rainfall) data 104 and the soil moisture data 106.

If, as illustrated via component 116, a soil water content increase is found, it implies that there is either rainfall (as illustrated by component 118) or an irrigation event (as illustrated by component 120). Here, the weather (rainfall) data 104 can help to distinguish soil water increment due to irrigation activity (component 120), thereby enabling identification of an irrigation date (as illustrated via component 126). Also, pixel-based identification can be performed for the region of interest to enable determination of the extent of irrigation (as also illustrated via component 126).

Figure 2:
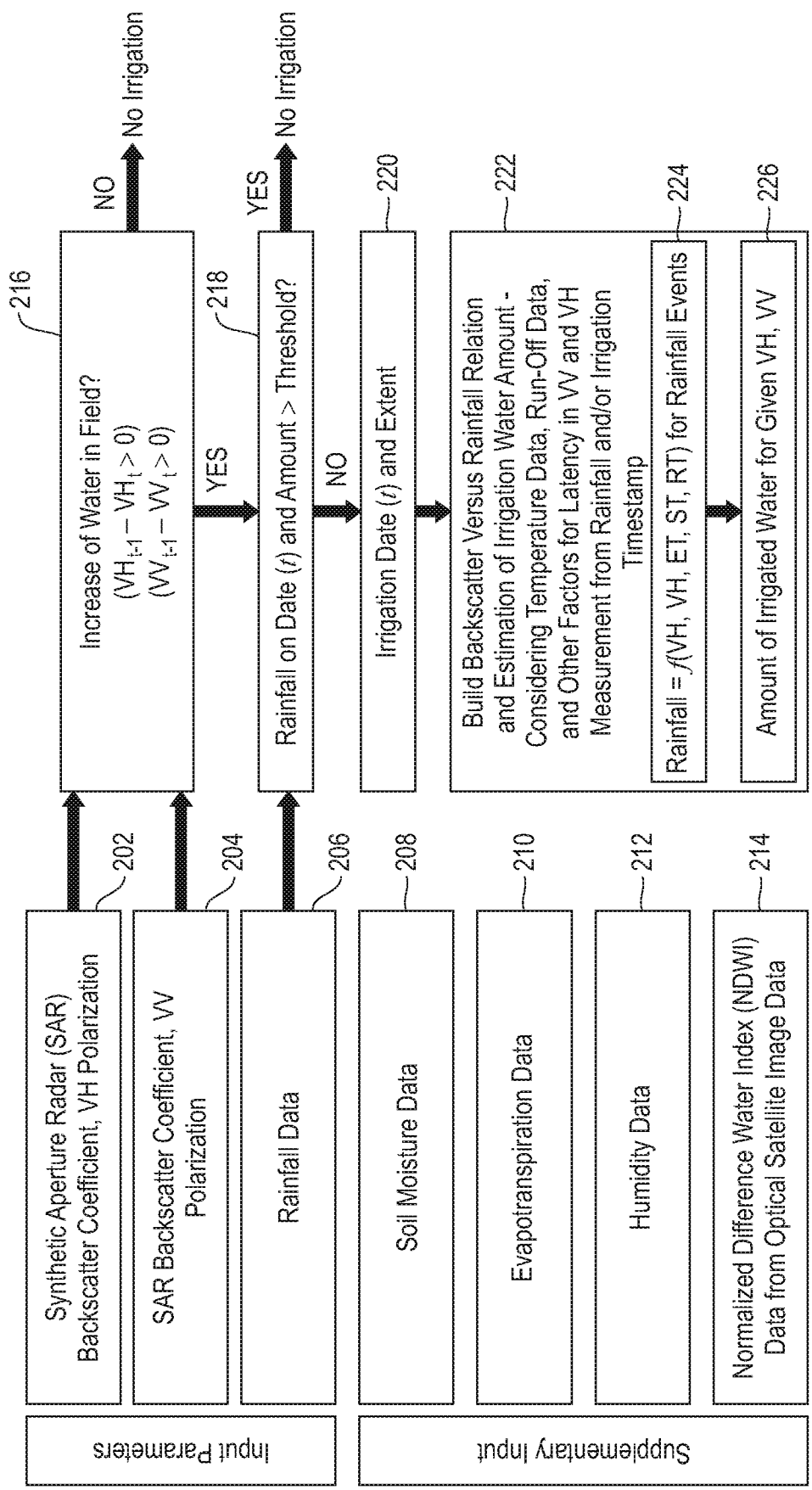
FIG. 2 is a diagram illustrating system architecture, according to an embodiment of the invention.

As also depicted in FIG. 1, a pre-trained machine learning model 130 (as further detailed, for example, in connection with component 226 in FIG. 2) estimates the amount of irrigated water (as illustrated via component 122) for given timestamp t using input features such as backscatter parameters 102, weather data 104 (e.g., evapotranspiration, temperature, humidity, etc.), and run-off and/or elevation map data 108. Another pre-trained machine learning model 132 is implemented to classify irrigation types (as illustrated via component 124) using input features such as backscatter parameters 102, normalized difference water index (NDWI) from optical satellite image data (further detailed in connection with component 214 in FIG. 2) and elevation map data 108. Accordingly, component 126 includes gridded irrigation information (timestamp, extent and amount of water) in a geographic information system, which then can be used as an input (as illustrated via component 128) for accurate estimation of soil moisture at field scale, as well as other agricultural applications such as a yield model, etc.

FIG. 2 is a diagram illustrating system architecture, according to an embodiment of the invention. By way of illustration, FIG. 2 depicts input parameters including synthetic aperture radar (SAR) backscatter parameter VH 202 and SAR backscatter parameter VV 204, which can include a positive difference for timestamps t and t−1, and are used to find an increase of soil water content via step 216 for timestamp t. Additionally, an input parameter of rainfall data 206 can be used to discriminate soil water content increases due to irrigation activities in step 218.

Supplementary inputs including soil moisture data 208, evapotranspiration data 210, and humidity data 212 (including for example, data pertaining to humidity increases due to irrigation) can be used to further confirm the estimation of irrigation events in connection with step 220. In addition, such data can also be used as input features in machine learning model 222 to account for total irrigated water estimation at timestamp t. Further, in connection with machine learning model 222, an estimated amount of rainfall is determined via step 224 and an estimated amount of irrigated water is determined via step 226. Also, normalized difference water index (NDWI) data 214 can be utilized in conjunction with the supplementary input, and can serve as portions of the input features for machine learning classification of different types of irrigation (such as detailed in connection with component 124 in FIG. 1). The NDWI data 214, in one or more embodiments, uses reflected near-infrared radiation and visible green light to enhance the presence of open water features while eliminating the presence of soil and vegetation features. NDWI returns a positive or close to zero value when water or wet soil features are encountered, and returns a negative value for dry soil and vegetation features.

Figure 3:
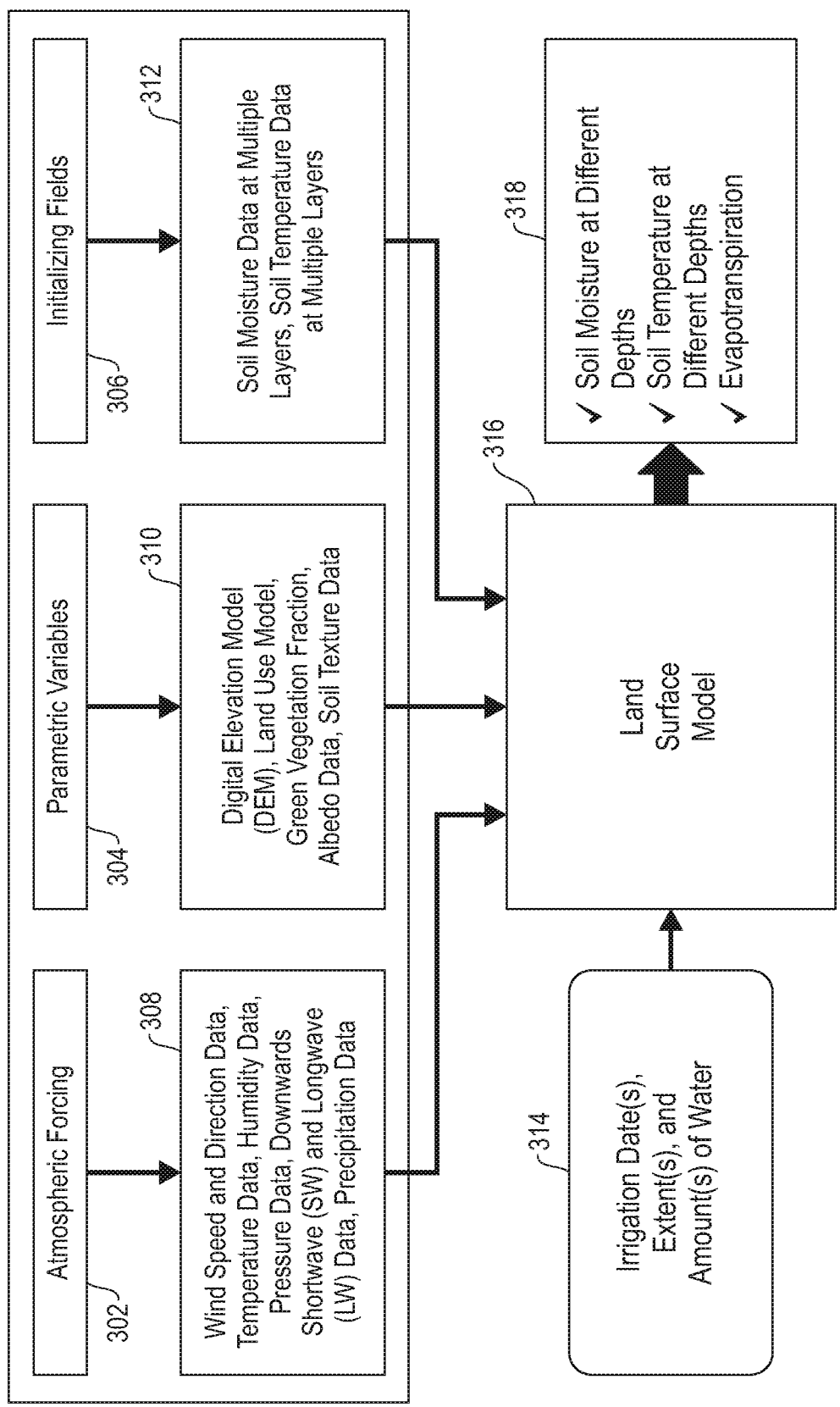
FIG. 3 is a diagram illustrating an example implementation of a land surface model, according to an exemplary embodiment of the invention.

FIG. 3 is a diagram illustrating an example implementation of a land surface model, according to an exemplary embodiment of the invention. By way of illustration, FIG. 3 depicts estimation of soil moisture using a land surface model 316 and a set of input parameters. Such parameters can include, for example, dynamic atmospheric forcing data 302 (also known as weather data) required at the land surface to simulate soil moisture, soil temperature at different depths, evapotranspiration, etc., wherein such data 302 can include specific variables 308 such as wind speed and direction data, temperature data, humidity data, pressure data, downwards shortwave (SW) and longwave (LW) data, and precipitation data. Such parameters can also include parametric variables 304, which can include specific variables 310 such as a digital elevation map (DEM), land use and land cover (LULC information), soil texture information, green vegetation fraction, surface albedo, etc. Additionally, such parameters can include initializing fields 306, which can include specific fields 312 such as soil moisture data and soil temperature data (at multiple layers) required to start a simulation at an initial model time.

As also depicted by FIG. 3, such parameters are input to land surface model 316 along with gridded irrigation data 314 (time stamp of an irrigation event, extent and amount of irrigation associated with the irrigation event, etc.), wherein the land surface model 316 processes such inputs and generates an output 318 that includes an estimation of soil moisture, soil temperature, and evapotranspiration information.

Figure 4:
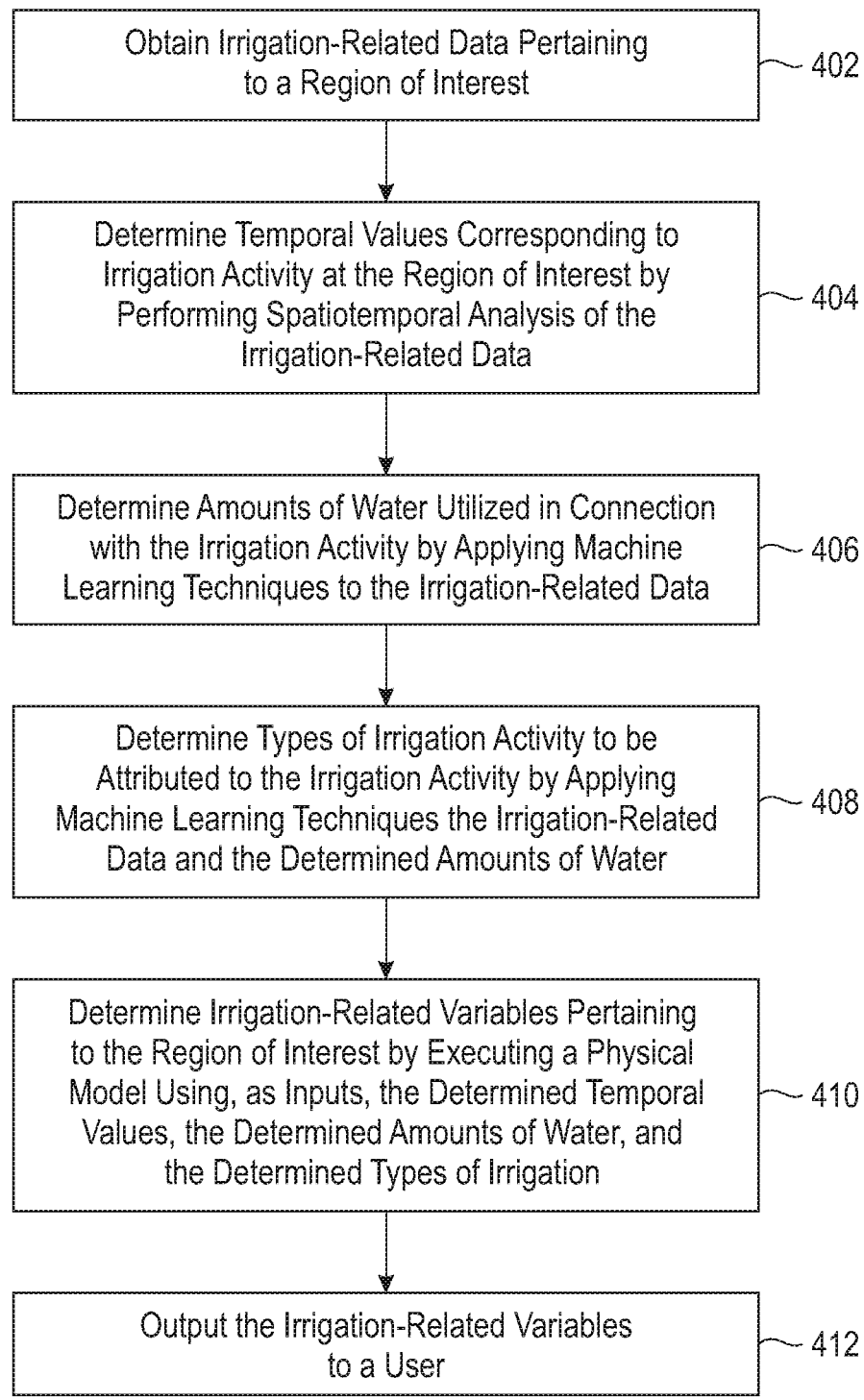
FIG. 4 is a flow diagram illustrating techniques according to an embodiment of the invention.

FIG. 4 is a flow diagram illustrating techniques according to an embodiment of the present invention. Step 402 includes obtaining multiple items of irrigation-related data pertaining to at least one region of interest. The multiple items of irrigation-related data can include one or more items of weather data, one or more items of multi spectral data (e.g., ranging across the electromagnetic spectrum), one or more items of hyperspectral data, one or more items of data pertaining to soil moisture, and/or one or more items of elevation data.

Step 404 includes determining one or more temporal values corresponding to irrigation activity at one or more portions of the at least one region of interest by performing spatiotemporal analysis of at least a portion of the obtained irrigation-related data. Performing spatiotemporal analysis can include performing spatiotemporal analysis of one or more backscattering parameters derived from the at least a portion of the obtained irrigation-related data.

Step 406 includes determining one or more amounts of water utilized in connection with the irrigation activity corresponding to the one or more determined temporal values by applying a first set of one or more machine learning techniques to at least a portion of the obtained irrigation-related data. Applying a first set of one or more machine learning techniques to at least a portion of the obtained irrigation-related data can include using one or more backscattering parameters derived from satellite data associated with the at least a portion of the obtained irrigation-related data.

Step 408 includes determining one or more types of irrigation activity to be attributed to the irrigation activity corresponding to the one or more determined temporal values by applying a second set of one or more machine learning techniques to (i) at least a portion of the obtained irrigation-related data and (ii) the one or more determined amounts of water utilized in connection with the irrigation activity. Determining one or more types of irrigation activity can include determining at least one pattern pertaining to one or more aspects of the obtained irrigation-related data. The at least one pattern pertaining to one or more aspects of the obtained irrigation-related data can include at least one surface-related pattern, at least one sprinkler-related pattern, at least one pivot-related pattern, at least one flood irrigation-related pattern, and/or at least one drip-related pattern. In one or more embodiments, the first set of one or more machine learning techniques can include the same one or more machine learning techniques as the second set, or can be distinct from the second set of one or more machine learning techniques. Further, in at least one embodiment, the one or more machine learning techniques can include at least one random forest algorithm, a support vector regression, and/or at least one neural network.

Step 410 includes determining one or more irrigation-related variables pertaining to the at least one region of interest by executing a physical model using, as inputs, (i) the one or more determined temporal values, (ii) the one or more determined amounts of water utilized in connection with the irrigation activity, and (iii) the one or more determined types of irrigation activity to be attributed to the irrigation activity, wherein the one or more irrigation-related variables comprises at least an extent of the irrigation activity. In one or more embodiments, determining the extent of irrigation activity enables the inclusion of information pertaining to how an entire region of interest (e.g., field, farm, etc.) was irrigated, which can then be utilized to identify one or more hot spots of low, optimal, and/or high irrigation areas in the region of interest using the determined irrigation date, irrigation type, and irrigation amount information. Also, in one or more embodiments, the one or more irrigation-related variables can also include soil moisture, soil temperature, and/or evapotranspiration. Step 412 includes outputting the one or more determined irrigation-related variables to at least one user.

As detailed herein, the techniques depicted in FIG. 4 can be carried out without the use of one or more sensors. Additionally, at least one embodiment includes performing one or more automated actions (e.g., outputting related information to at least one user, modifying one or more irrigation parameters and/or configurations in connection with irrigation activity, etc.) in response to (i) the one or more determined temporal values, (ii) the one or more determined amounts of water utilized in connection with the irrigation activity, (iii) the one or more determined types of irrigation activity to be attributed to the irrigation activity, and (iv) the determined extent of the irrigation activity.

The techniques depicted in FIG. 4 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an embodiment of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 4 can be implemented via a computer program product that can include computer useable program code that is stored in a computer readable storage medium in a data processing system, and wherein the computer useable program code was downloaded over a network from a remote data processing system. Also, in an embodiment of the invention, the computer program product can include computer useable program code that is stored in a computer readable storage medium in a server data processing system, and wherein the computer useable program code is downloaded over a network to a remote data processing system for use in a computer readable storage medium with the remote system.

An embodiment of the invention or elements thereof can be implemented in the form of an apparatus including a memory and at least one processor that is coupled to the memory and configured to perform exemplary method steps.

Figure 5:
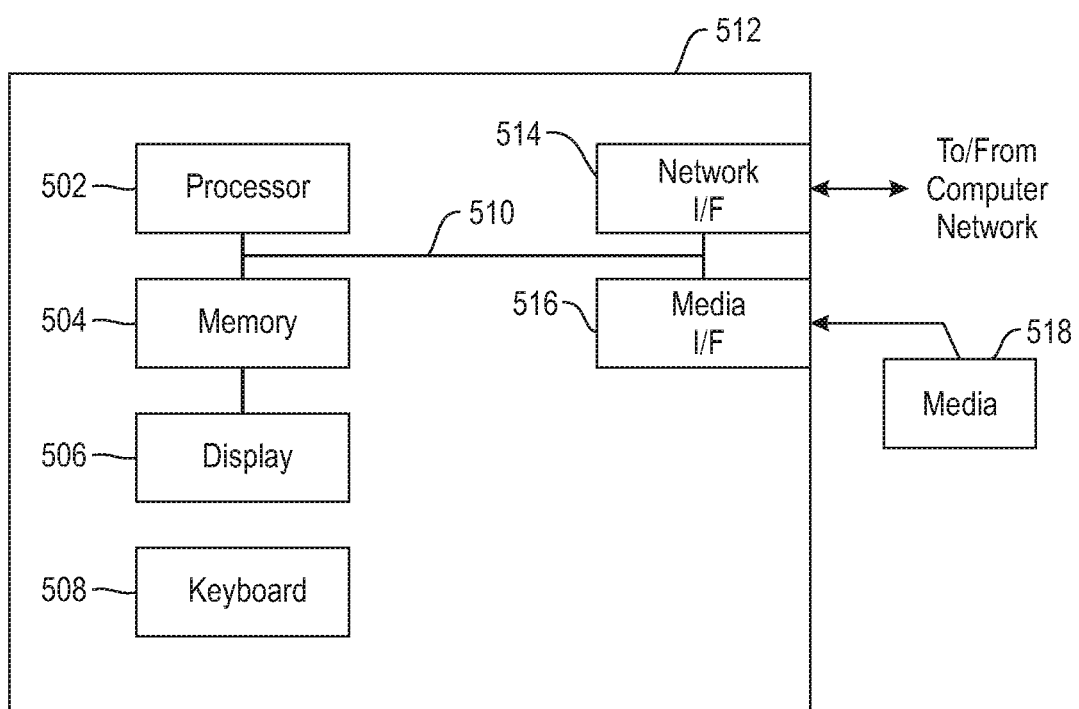
FIG. 5 is a system diagram of an exemplary computer system on which at least one embodiment of the invention can be implemented.

Additionally, an embodiment of the present invention can make use of software running on a computer or workstation. With reference to FIG. 5, such an implementation might employ, for example, a processor 502, a memory 504, and an input/output interface formed, for example, by a display 506 and a keyboard 508. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 502, memory 504, and input/output interface such as display 506 and keyboard 508 can be interconnected, for example, via bus 510 as part of a data processing unit 512. Suitable interconnections, for example via bus 510, can also be provided to a network interface 514, such as a network card, which can be provided to interface with a computer network, and to a media interface 516, such as a diskette or CD-ROM drive, which can be provided to interface with media 518.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 502 coupled directly or indirectly to memory elements 504 through a system bus 510. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including, but not limited to, keyboards 508, displays 506, pointing devices, and the like) can be coupled to the system either directly (such as via bus 510) or through intervening I/O controllers (omitted for clarity).

Network adapters such as network interface 514 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "server" includes a physical data processing system (for example, system 512 as shown in FIG. 5) running a server program. It will be understood that such a physical server may or may not include a display and keyboard.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 502. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed digital computer with associated memory, and the like. Given the teachings of the invention provided herein, one of ordinary skill in the related art will be able to contemplate other implementations of the components of the invention.

Additionally, it is understood in advance that implementation of the teachings recited herein are not limited to a particular computing environment. Rather, embodiments of the present invention are capable of being implemented in conjunction with any type of computing environment now known or later developed.

For example, cloud computing is a model of service delivery for enabling convenient, on-demand network access to a shared pool of configurable computing resources (for example, networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (for example, country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (for example, storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (for example, web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (for example, host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (for example, mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (for example, cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
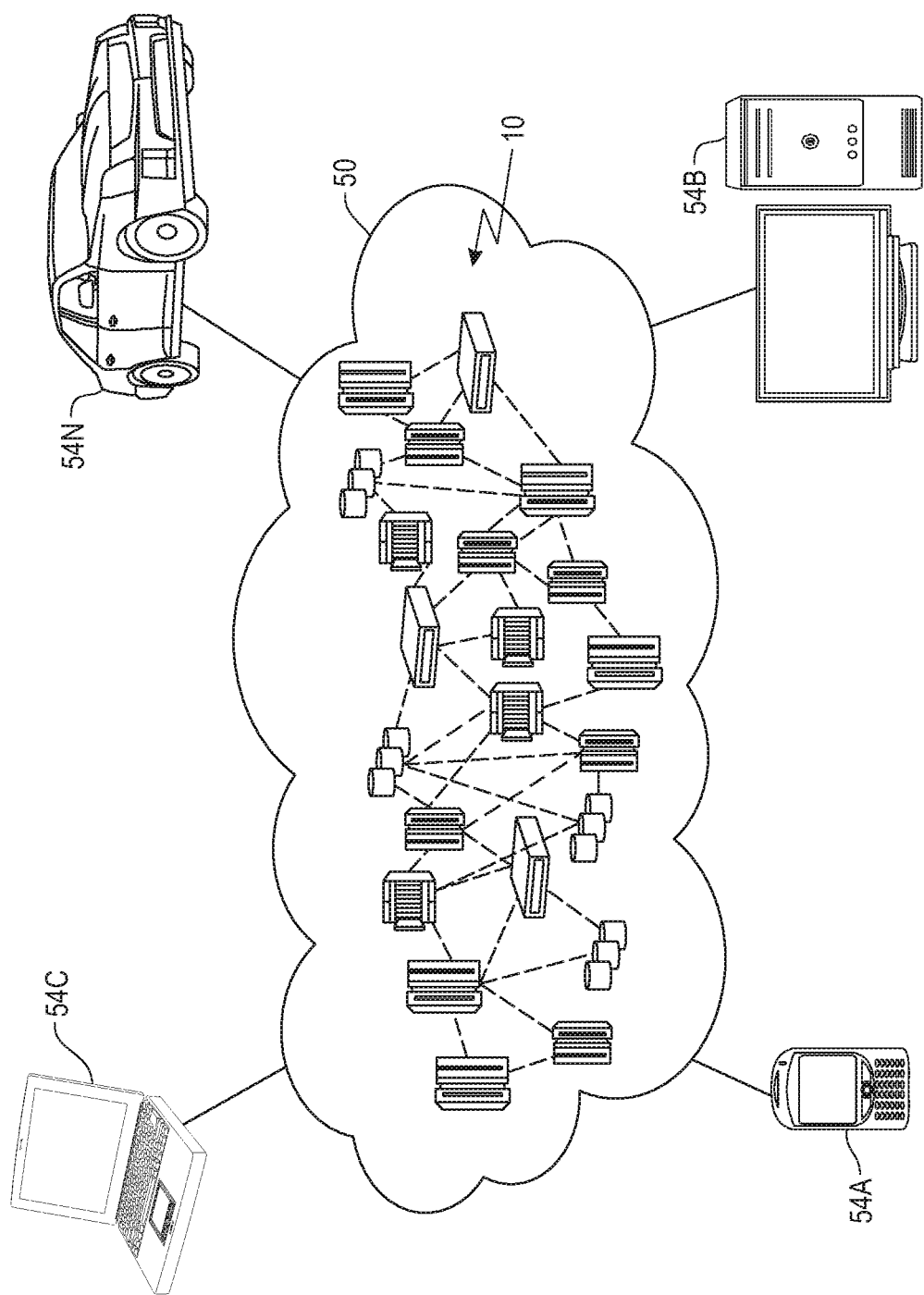
FIG. 6 depicts a cloud computing environment according to an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
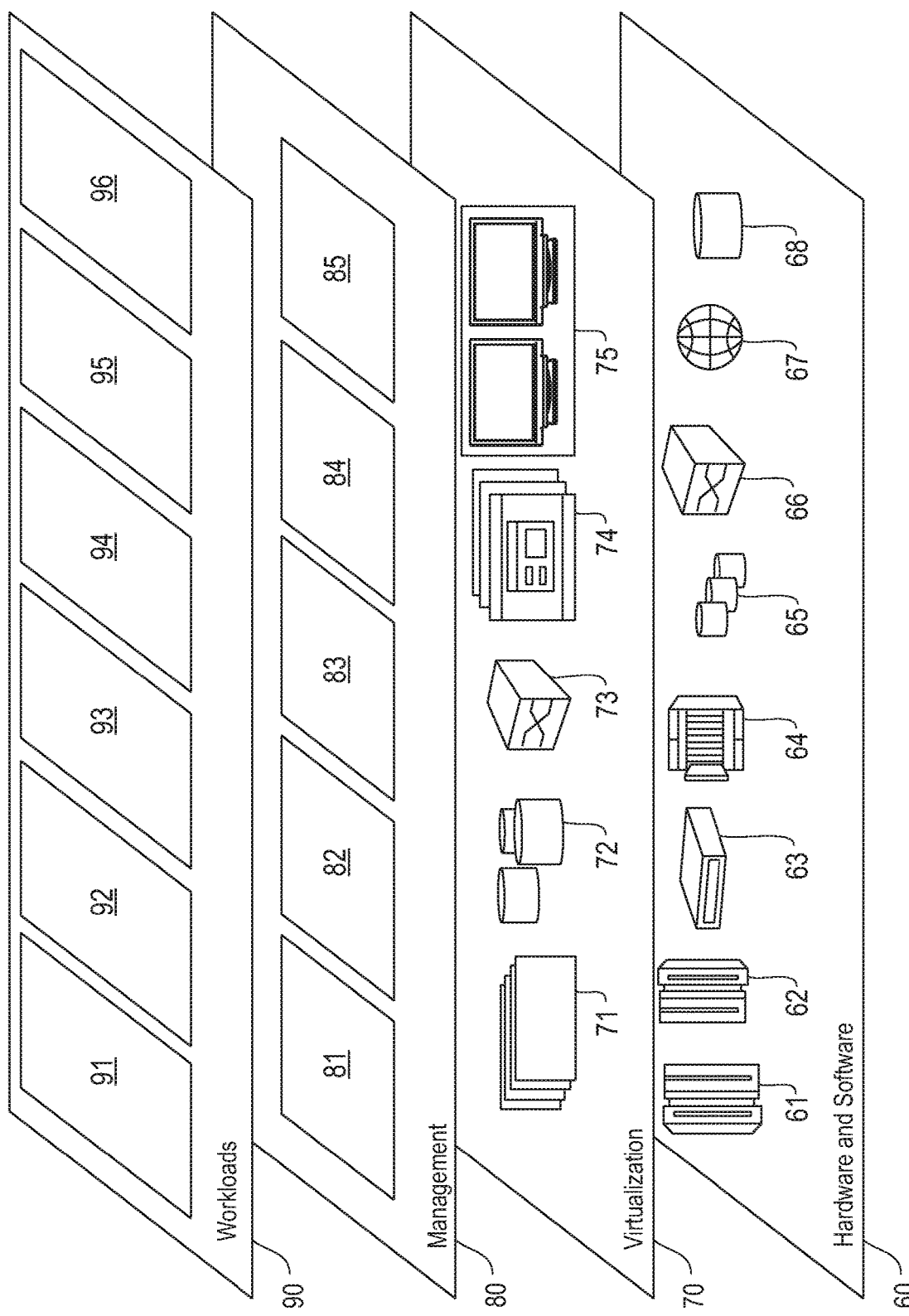
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75. In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources.

In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and irrigation-related data determination 96, in accordance with the one or more embodiments of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, improving the accuracy of models that provide estimates of agronomic factors, while also reducing dependence on cost- and maintenance-intensive sensors and monitoring systems.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   obtaining multiple items of irrigation-related data pertaining to at least one region of interest;
   determining one or more temporal values corresponding to irrigation activity at one or more portions of the at least one region of interest by performing spatiotemporal analysis of at least a portion of the obtained irrigation-related data;
   determining one or more amounts of water utilized in connection with the irrigation activity corresponding to the one or more determined temporal values by applying a first set of one or more machine learning techniques to at least a portion of the obtained irrigation-related data;
   determining one or more types of irrigation activity to be attributed to the irrigation activity corresponding to the one or more determined temporal values by applying a second set of one or more machine learning techniques to (i) at least a portion of the obtained irrigation-related data and (ii) the one or more determined amounts of water utilized in connection with the irrigation activity;
   determining one or more irrigation-related variables pertaining to the at least one region of interest by executing a physical model using, as inputs, (i) the one or more determined temporal values, (ii) the one or more determined amounts of water utilized in connection with the irrigation activity, and (iii) the one or more determined types of irrigation activity to be attributed to the irrigation activity, wherein the one or more irrigation-related variables comprises at least an extent of the irrigation activity; and
   outputting the one or more determined irrigation-related variables to at least one user;
   wherein the method is carried out by at least one computing device.

2. The computer-implemented method of claim 1, wherein the method is carried out without the use of one or more sensors.

3. The computer-implemented method of claim 1, wherein said performing spatiotemporal analysis comprises performing spatiotemporal analysis of one or more backscattering parameters derived from microwave satellite data associated with the at least a portion of the obtained irrigation-related data.

4. The computer-implemented method of claim 1, wherein said applying a first set of one or more machine learning techniques to at least a portion of the obtained irrigation-related data comprises using one or more backscattering parameters derived from microwave satellite data associated with the at least a portion of the obtained irrigation-related data.

5. The computer-implemented method of claim 1, wherein said determining one or more types of irrigation activity comprises determining at least one pattern pertaining to one or more aspects of the obtained irrigation-related data.

6. The computer-implemented method of claim 5, wherein the at least one pattern pertaining to one or more aspects of the obtained irrigation-related data comprises at least one surface-related pattern.

7. The computer-implemented method of claim 5, wherein the at least one pattern pertaining to one or more aspects of the obtained irrigation-related data comprises at least one of a sprinkler-related pattern, a pivot-related pattern, and a flood irrigation-related pattern.

8. The computer-implemented method of claim 5, wherein the at least one pattern pertaining to one or more aspects of the obtained irrigation-related data comprises at least one drip-related pattern.

9. The computer-implemented method of claim 1, wherein the multiple items of irrigation-related data comprise one or more items of weather data.

10. The computer-implemented method of claim 1, wherein the multiple items of irrigation-related data comprise one or more items of multispectral data ranging across the electromagnetic spectrum.

11. The computer-implemented method of claim 1, wherein the multiple items of irrigation-related data comprise one or more items of hyperspectral data.

12. The computer-implemented method of claim 1, wherein the multiple items of irrigation-related data comprise one or more items of elevation data.

13. The computer-implemented method of claim 1, wherein the multiple items of irrigation-related data comprise one or more items of data pertaining to soil moisture.

14. The computer-implemented method of claim 1, wherein the one or more irrigation-related variables comprises at least one of soil temperature and evapotranspiration.

15. The computer-implemented method of claim 1, wherein the one or more machine learning techniques comprises at least one random forest algorithm.

16. The computer-implemented method of claim 1, wherein the one or more machine learning techniques comprises a support vector regression.

17. The computer-implemented method of claim 1, wherein the one or more machine learning techniques comprises at least one neural network.

18. A computer program product comprising a computer readable storage medium having program instructions embodied therewith, the program instructions executable by a computing device to cause the computing device to:
   obtain multiple items of irrigation-related data pertaining to at least one region of interest;
   determine one or more temporal values corresponding to irrigation activity at one or more portions of the at least one region of interest by performing spatiotemporal analysis of at least a portion of the obtained irrigation-related data;
   determine one or more amounts of water utilized in connection with the irrigation activity corresponding to the one or more determined temporal values by applying a first set of one or more machine learning techniques to at least a portion of the obtained irrigation-related data;
   determine one or more types of irrigation activity to be attributed to the irrigation activity corresponding to the one or more determined temporal values by applying a second set of one or more machine learning techniques to (i) at least a portion of the obtained irrigation-related data and (ii) the one or more determined amounts of water utilized in connection with the irrigation activity;
   determine one or more irrigation-related variables pertaining to the at least one region of interest by executing a physical model using, as inputs, (i) the one or more determined temporal values, (ii) the one or more determined amounts of water utilized in connection with the irrigation activity, and (iii) the one or more determined types of irrigation activity to be attributed to the irrigation activity, wherein the one or more irrigation-related variables comprises at least an extent of the irrigation activity; and
   output the one or more determined irrigation-related variables to at least one user.

19. A system comprising:
   a memory; and
   at least one processor operably coupled to the memory and configured for:
      obtaining multiple items of irrigation-related data pertaining to at least one region of interest;
      determining one or more temporal values corresponding to irrigation activity at one or more portions of the at least one region of interest by performing spatiotemporal analysis of at least a portion of the obtained irrigation-related data;
      determining one or more amounts of water utilized in connection with the irrigation activity corresponding to the one or more determined temporal values by applying a first set of one or more machine learning techniques to at least a portion of the obtained irrigation-related data;
      determining one or more types of irrigation activity to be attributed to the irrigation activity corresponding to the one or more determined temporal values by applying a second set of one or more machine learning techniques to (i) at least a portion of the obtained irrigation-related data and (ii) the one or more determined amounts of water utilized in connection with the irrigation activity;
      determining one or more irrigation-related variables pertaining to the at least one region of interest by executing a physical model using, as inputs, (i) the one or more determined temporal values, (ii) the one or more determined amounts of water utilized in connection with the irrigation activity, and (iii) the one or more determined types of irrigation activity to be attributed to the irrigation activity, wherein the one or more irrigation-related variables comprises at least an extent of the irrigation activity; and
      outputting the one or more determined irrigation-related variables to at least one user.

20. A computer-implemented method comprising:
   determining one or more temporal values corresponding to irrigation activity at one or more portions of at least one region of interest by performing spatiotemporal analysis of one or more backscattering parameters derived from microwave satellite data associated with irrigation-related data;
   determining one or more amounts of water utilized in connection with the irrigation activity corresponding to the one or more determined temporal values by applying a first set of one or more machine learning techniques to at least a portion of the irrigation-related data and the one or more backscattering parameters;
   determining one or more types of irrigation activity to be attributed to the irrigation activity corresponding to the one or more determined temporal values by applying a second set of one or more machine learning techniques to (i) at least a portion of the irrigation-related data and (ii) the one or more determined amounts of water utilized in connection with the irrigation activity;
   determining an extent of the irrigation activity by executing a physical model using, as inputs, (i) the one or more determined temporal values, (ii) the one or more determined amounts of water utilized in connection with the irrigation activity, and (iii) the one or more determined types of irrigation activity to be attributed to the irrigation activity; and
   performing one or more automated actions in response to (i) the one or more determined temporal values, (ii) the one or more determined amounts of water utilized in connection with the irrigation activity, (iii) the one or more determined types of irrigation activity to be attributed to the irrigation activity, and (iv) the determined extent of the irrigation activity;

wherein the method is carried out by at least one computing device.

* * * * *